US00PP35717P2

(12) United States Plant Patent
Kraan

(10) Patent No.: US PP35,717 P2
(45) Date of Patent: Apr. 2, 2024

(54) ***HYDRANGEA* PLANT NAMED 'BOCOTOSO'**

(50) Latin Name: *Hydrangea quercifolia*
Varietal Denomination: Bocotoso

(71) Applicant: Kees Jan Kraan, Alphen aan den Rijn (NL)

(72) Inventor: Kees Jan Kraan, Alphen aan den Rijn (NL)

(73) Assignees: BOOT & CO BOOMKWEKERIJEN BV, Boskoop (NL), part interest; KOLSTER BV, Boskoop (NL), part interest ( * ) Notice: Subject to any disclaimer, the term of this patent is extended or adjusted under 35 U.S.C. 154(b) by 362 days.

(21) Appl. No.: 17/864,759

(22) Filed: Jul. 14, 2022

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hydrangea quercifolia* plant named 'Bocotoso' that is characterized by its inflorescences with fertile and sterile flowers, its small, dense, compact plant habit, its strong branches (do not lodge), its red foliage colors in late summer to early fall, its dense inflorescences that are ovate to conical in shape with white sterile flowers, and its floriferous blooming habit.

3 Drawing Sheets

Botanical classification: *Hydrangea quercifolia.*
Varietal denomination: 'Bocotoso'.

BACKGROUND OF THE INVENTION

The present invention relates to a new and distinct cultivar of *Hydrangea quercifolia* and will be referred to hereafter by its cultivar name, 'Bocotoso'. 'Bocotoso' represents a new oak leaf *Hydrangea*, a perennial shrub grown for landscape use.

'Bocotoso' was derived from an ongoing breeding program by the Inventor in Boskoop, The Netherlands. 'Bocotoso' arose from open pollination of *Hydrangea quercifolia* 'Sikes Dwarf' (not patented) in July of 2009. The male parent is therefore unknown. 'Bocotoso' was selected as a single unique plant from amongst the resulting seedlings in August of 2021.

Asexual propagation of the new cultivar was first accomplished by stem cuttings by the Inventor in 2016 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bocotoso' as a unique cultivar of *Hydrangea quercifolia.*

1. 'Bocotoso' exhibits inflorescences with fertile and sterile flowers.
2. 'Bocotoso' exhibits a small, dense, compact plant habit.
3. 'Bocotoso' exhibits strong branches (do not lodge).
4. 'Bocotoso' exhibits red foliage colors in late summer to early fall.

5. 'Bocotoso' exhibits dense inflorescences that are ovate to conical in shape with white sterile flowers.
6. 'Bocotoso' exhibits a floriferous blooming habit.

The female parent of 'Bocotoso' differs from 'Bocotoso' in having a smaller plant size, weaker branches, and foliage that turns red later in the season. 'Bocotoso' can be most compared to *Hydrangea quercifolia* cultivars 'Munchkin' (Not patented) and 'Ruby Slippers' (not patented). Both are similar to 'Bocotoso' in having a small, dense, compact plant habit. 'Munchkin' differs from 'Bocotoso' in having inflorescences that turn medium pink in color when they mature and lighter green foliage that turns red later in fall. 'Ruby Slippers' differs from 'Bocotoso' in having inflorescences that turn red in color when they mature and lighter green foliage that turns red later in fall.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include a website listings by Blooming Easy Wholesale.

BRIEF DESCRIPTION OF THE DRAWINGS

The accompanying color photographs illustrate the overall appearance and distinct characteristics of the new

*Hydrangea*. The photographs were taken of a plant two years in age as grown outdoors in a 2-gallon container in Abbotsford, B.C., Canada.

Figure 1:
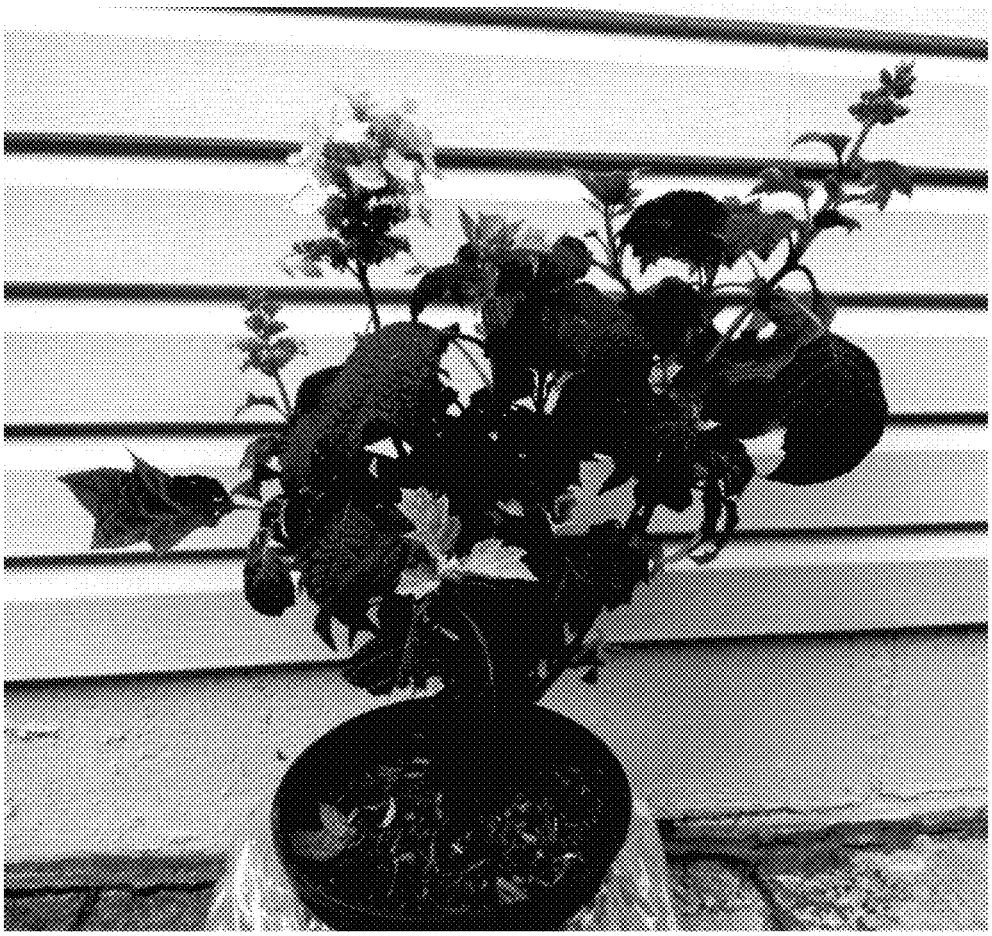

The photograph in FIG. 1 provides a side view of the plant habit of 'Bocotoso' in bloom.

Figure 2:
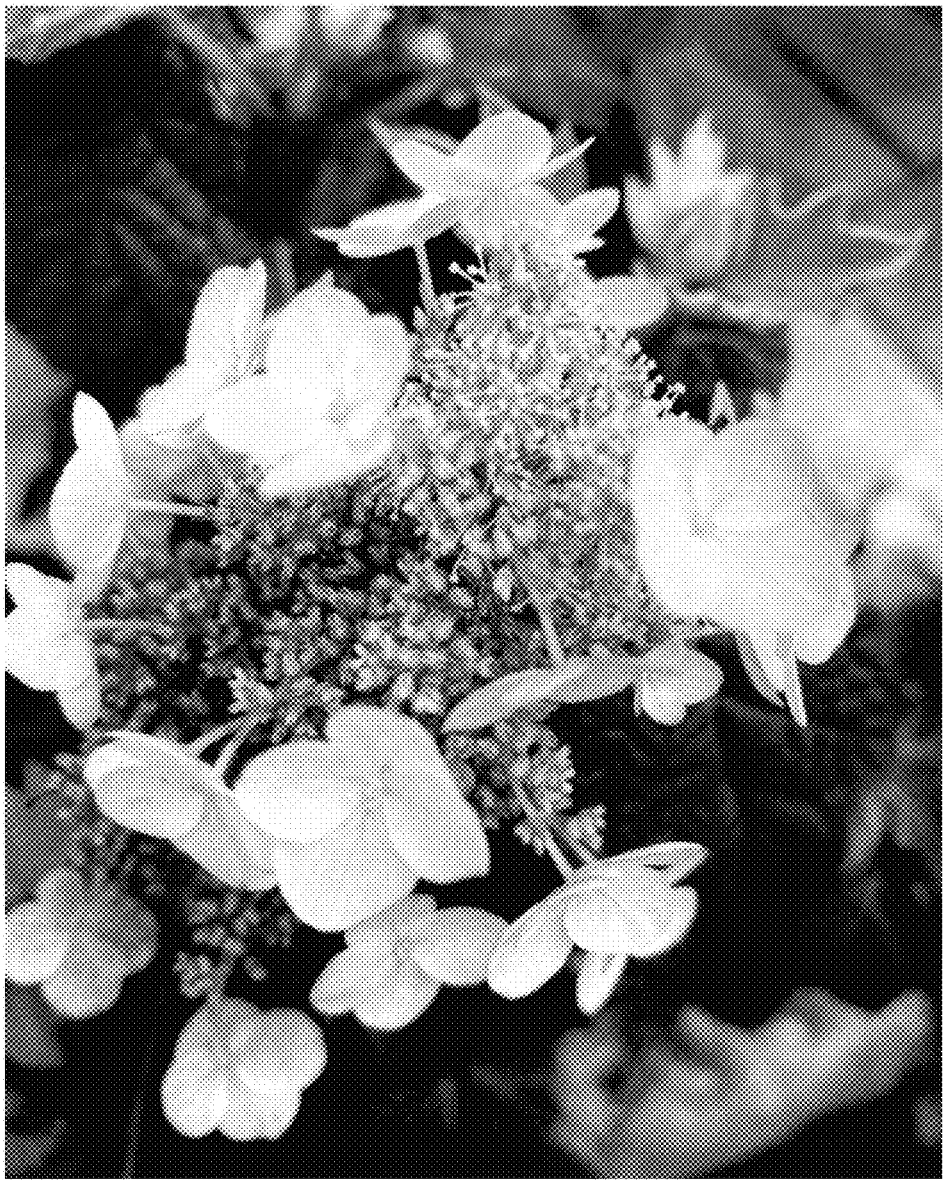

The photograph in FIG. 2 provides a close-up view of a fully open inflorescence of 'Bocotoso'.

Figure 3:
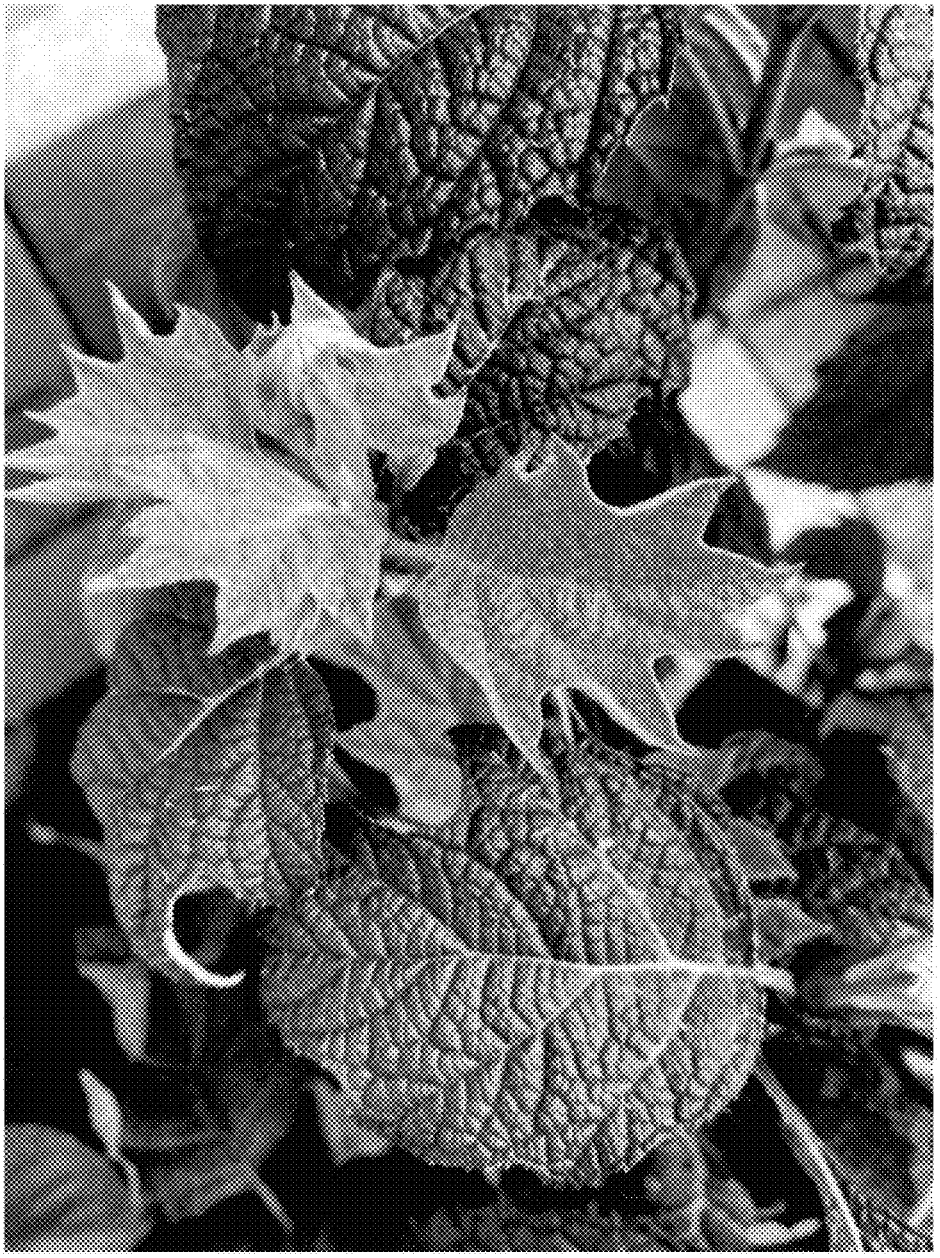

The photograph in FIG. 3 provides a close-up view of the foliage of 'Bocotoso'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown outdoors in 2-gallon containers in Abbotsford, B.C., Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Average of 6 weeks, early summer into late summer in The Netherlands.

*Plant type.*—Perennial flowering shrub.

*Plant habit.*—Compact, sturdy upright stems.

*Height and spread.*—An average of 42 cm in height (foliar height), 51 cm (floral height), 54 cm in width (as a 2-year-old plant), an average of 1.25 m in height and spread as a mature plant in the landscape.

*Hardiness.*—At least in U.S.D.A. Zones 6 to 9.

*Diseases and pests.*—No susceptibility and resistance to pests and diseases has been observed.

*Root description.*—Fibrous, 163B and 161D.

*Time required for root development.*—2 to 4 weeks for root initiation with a flowering plant finished in one to two years.

*Growth rate.*—Low to moderate.

Stem description:

*Stem shape.*—Rounded, slightly oval.

*Stem color.*—New growth; 145A, densely covered with woolly pubescence 167A, mature stems; 180A, densely covered with woolly pubescence 167A, bark; 199B and 164A in color.

*Stem size.*—Main branch (trunk); 6 cm in length, 1.5 cm in diameter, lateral branches, 38 cm in length, 4 mm in diameter.

*Stem surface.*—Densely pubescent, bark; medium, exfoliating towards the base.

*Stem aspect.*—Average angle 60° to 90° (soil level=0°).

*Internode length.*—1 to 5 cm.

*Branching.*—Average of 5 lateral branches from main stem.

*Stem strength.*—Strong.

Foliage description:

*Leaf shape.*—Oak-leaf, ovate to slightly oblong in overall form.

*Leaf division.*—Simple.

*Leaf size.*—Up to 12 cm in length and 8 cm in width.

*Leaf base.*—Acute.

*Leaf apex.*—Acute with apex of lobes acute.

*Leaf venation.*—Pinnate, upper surface veins recessed, matte, young; upper veins a blend of 163C and 167A in color, lower veins raised 159A in color, densely covered with fine, woolly pubescence average of 1 mm in length and 164A in color, mature; upper veins 161B in color, lower veins raised and glossy, N148A in color, flushed with 173A in color and densely covered with fine, woolly pubescence average of 2 mm in length and 155C in color.

*Leaf margins.*—3-lobed with lobes serrate with very tip of serrations mucronate, lobes are moderately deeply lobed with sinuses on mature leaves ranging from 0.5 mm to 1 cm in depth.

*Leaf attachment.*—Petiolate.

*Leaf arrangement.*—Opposite.

*Leaf surface.*—New growth upper surface; heavily coated with dense woolly pubescence 192D in color, matte, new growth lower surface; heavily coated with dense woolly pubescence 157D in color, matte, mature leaves upper surface; moderately glossy, rugose, and sparsely covered with short, stiff hairs, NN155C in color, 0.3 mm in length, mature leaves lower surface; heavily coated with woolly pubescence 157A in color, matte.

*Leaf color.*—Immature leaves upper surface; 157C and 143A, as the leaf develops changing to 137A, immature leaves lower surface; 193A, as the leaf develops changing to 191A, mature leaves upper surface; 200B, mature leaves lower surface; N148A, mature and fall leaves upper surface; a blend of 200A and N34A, mature and fall leaves lower surface; a blend of 48A and 177A.

*Petioles.*—Up to 5 cm in length and 2 mm in diameter, upper surface; flat to slightly channeled, moderate in strength, held in multiple angles slightly upward to slightly and moderately pendulant, young; upper side a blend of 163C and 167A in color, lower side 159A in color, densely covered with fine, woolly pubescence average of 1 mm in length and 164A and 169A in color, mature; upper side 161B in color, lower side glossy, N148A in color, flushed with 173A in color and densely covered with fine, woolly pubescence average of 2 mm in length and 155C in color.

Inflorescence description:

*Inflorescence type.*—Terminal panicle, comprised of sterile and fertile flowers.

*Lastingness of inflorescence.*—Up to 10 weeks.

*Inflorescence number.*—One per lateral stem.

*Inflorescence size.*—Average of 12 cm in height and 9 cm in diameter.

*Inflorescence bracts.*—An average of 2, up to 1 cm in length and 3 mm in width, elliptic in shape, apex acute, base cuneate, margin entire to very slightly serrate, surfaces matte, color; 145A, flushed with 179B.

*Flower fragrance.*—Very pleasant and moderately strong fragrance.

*Flower buds.*—Sterile flowers; an average of 1 mm in length and 1.2 mm in diameter, ovate in shape, 155B in color, flushed with 179A in color, glabrous and matte surface, fertile flowers; an average of 2 mm in length and 1.1 mm in diameter, oval to flattened globular in shape, 145A in color, flushed with 179A in color at the very top middle, glabrous and matte surface.

*Sterile flowers.*—Average of 22 per inflorescence, rotate, held outward, 1 mm in depth, 2 cm in diameter.

*Fertile flowers.*—An average of 200 per inflorescence, closed campanulate in shape, held at all angles, 4 mm in depth, 1.2 cm in diameter.

*Peduncles.*—Strong, up to 1.5 cm in length and 1 mm in width, 144A in color, surface sparsely covered with fine woolly pubescence, 164A and 169A in color.

*Pedicels.*—Average of 2 to 5 mm in length, 0.5 mm in diameter, moderately strong, 144A in color, surface sparsely covered with fine woolly pubescence, 164A and 169A in color.

*Petals.*—Sterile flowers; petals drop when opening, fertile flowers; when opening upper and lower surface; 157A, flushed with 182A, when fully open upper and lower surface; petals drop when mature.

*Sepals.*—Sterile flowers; showy, 4, whorl arrangement, ovate in shape, entire to slightly undulate margins, bluntly acute to rounded apex, acute base, upper and lower surface glabrous and matte, color; upper and lower surface when opening; base to mid-section 143A, tips 145B to 145C, upper and lower surface when fully open; NN155A, center sepals 144A, color when maturing upper and lower surface; 155A, as the sepals start to fade becoming flushed with 49A, fertile flowers; 4, rotate in arrangement, elliptic in shape, acute apex, cuneate base, entire margin, an average of 2 mm in length and 1 mm in width, both surfaces glabrous and matte, upper and lower surface 178A in color.

Reproductive organs:

*Stamens.*—Sterile flowers; average of 6, filament is 1.5 mm in length and 155A in color, anther is globular in shape, 0.5 mm in diameter and 160B in color, sometimes slightly tinted with 150A in color, pollen is very low in quantity and too minimal for color reading, fertile flowers; average of 9, filament is 3 mm in length and NN155B in color, anther is orbicular and 2-parted in shape, 1 mm in diameter and 158A in color, pollen is very low in quantity and too minimal for color reading.

*Pistils.*—Sterile flowers; very minute, 2, style and stigma non-distinguishable, 0.5 mm in diameter, 155A in color, fertile flowers; 2, style is an average of 0.5 mm in length and 150D in color, stigma is 1 mm in diameter and 150D in color as it matures turning 160B in color, ovary is 150C in color, round and 1 mm in diameter.

*Fruit and seed.*—No fruit or seed production has been observed.

It is claimed:

1. A new and distinct cultivar of *Hydrangea* plant named 'Bocotoso' substantially as herein illustrated and described.

* * * * *